United States Patent
Boije et al.

(10) Patent No.: US 6,531,622 B1
(45) Date of Patent: Mar. 11, 2003

(54) CRYTALLINE FORM OF (S)-2 ETHOXY -3-[4-(2-{4- METHANESULFONYLOXYPHENYL} ETHOXY)PHENYL]PROPANOIC ACID

(75) Inventors: Maria Boije, Mölndal (SE); Karol Horvath, Södertälje (SE); Tord Inghardt, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/148,821

(22) PCT Filed: Nov. 29, 2000

(86) PCT No.: PCT/SE00/02384

§ 371 (c)(1), (2), (4) Date: Jun. 3, 2002

(87) PCT Pub. No.: WO01/40171

PCT Pub. Date: Jun. 7, 2001

(30) Foreign Application Priority Data

Dec. 3, 1999 (SE) ................................................ 9904416
Apr. 3, 2000 (SE) ................................................ 0001187

(51) Int. Cl.⁷ ......................... A61K 31/255; A61P 3/10; C07C 309/66
(52) U.S. Cl. ......................................... 558/44; 514/517
(58) Field of Search ............................ 558/44; 514/517

(56) References Cited

U.S. PATENT DOCUMENTS 6,258,850 B1 * 7/2001 Anderson .................... 514/571

FOREIGN PATENT DOCUMENTS

| WO | 9962871 | 12/1999 |
| WO | 9962872 | 12/1999 |

* cited by examiner

*Primary Examiner*—Robert W. Ramsuer
(74) *Attorney, Agent, or Firm*—White & Case LLP

(57) ABSTRACT

The present invention relates to a novel crystalline form of the compound (S)-2-ethoxy-3-[4-(2-{4-methanesulfonyloxyphenyl}ethoxy)phenyl]propanoic acid, shown by formula (I), or a pharmaceutically-acceptable salt thereof, and solvates thereof. The invention also concerns methods of treating one or more metabolic disease conditions, particularly those associated with Insulin Resistance Syndrome, and the use of a crystalline form of the compound, or a pharmaceutically-acceptable salt thereof, or a solvate thereof, in the manufacture of a medicament for use in one or more of said conditions. The invention further concerns pharmaceutical compositions containing a crystalline form of the compound, or a pharmaceutically-acceptable salt thereof, or a solvate thereof, as active ingredient, as well as processes for the manufacture of a crystalline form of the compound, or a pharmaceutically-acceptable salt thereof, or a solvate thereof.

5 Claims, No Drawings

CRYTALLINE FORM OF (S)-2 ETHOXY -3-[4-(2-{4- METHANESULFONYLOXYPHENYL} ETHOXY)PHENYL]PROPANOIC ACID

The present invention relates to a crystalline form of the compound (S)-2-ethoxy-3-[4-(2-{4-methanesulfonyloxyphenyl}ethoxy)phenyl] propanoic acid as shown in formula I below

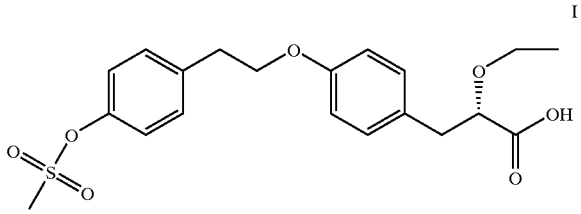

or a pharmaceutically-acceptable salt thereof, and solvates thereof. The invention also concerns methods of treating one or more metabolic disease conditions, particularly those associated with Insulin Resistance Syndrome, and the use of a crystalline form of the compound, or a pharmaceutically-acceptable salt thereof, or a solvate thereof, in the manufacture of a medicament for therapeutic use in one or more of said metabolic diseases.

The invention further concerns pharmaceutical compositions containing a crystalline form of the compound, or a pharmaceutically-acceptable salt thereof, or a solvate thereof, as active ingredient, as well as processes for the manufacture of a crystalline form of the compound, or a pharmaceutically-acceptable salt thereof, or a solvate thereof.

In the formulation of drug compositions, it is important for the drug substance to be in a form in which it can be conveniently handled and processed. This is of importance, not only from the point of view of obtaining a commercially viable manufacturing process, but also from the point of subsequent manufacture of pharmaceutical formulations comprising the active compound.

Chemical stability, solid state stability, and shelf life of the active ingredients are also very important factors. The drug substance, and compositions containing it, should be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically-pure as possible.

Amorphous materials may present significant problems in this regard. For example, such materials are typically more difficult to handle and to formulate than crystalline material, provide for unreliable solubility, and are often found to be unstable and chemically impure.

The skilled person will appreciate that, if a drug can be readily obtained in a stable crystalline form, the above problems may be solved.

Thus, in the manufacture of commercially viable, and pharmaceutically acceptable, drug compositions, it is desirable, wherever possible, to provide drug in a substantially crystalline, and stable, form.

It is to be noted, however, that this goal is not always achievable. Indeed, typically, it is not possible to predict, from molecular structure alone, what the crystallisation behaviour of a compound will be, and this can usually only be determined empirically.

The above compound is intended for therapeutic use in Insulin Resistance Syndrome (IRS), which refers to a cluster of manifestations including insulin resistance with accompanying hyperinsulinaemia, possible type 2 diabetes mellitus, arterial hypertension, central (visceral) obesity, dyslipidaemia observed as deranged lipoprotein levels typically characterised by elevated VLDL (very low density lipoproteins) and reduced HDL (high density lipoproteins) concentrations and reduced fibrinolysis.

Recent epidemiological research has documented that individuals with insulin resistance run a greatly increased risk of cardiovascular morbidity and mortality, notably suffering from myocardial infarction and stroke. In type 2 diabetes mellitus atherosclerosis related conditions cause up to 80% of all deaths.

In clinical medicine there is awareness of the need to increase the insulin sensitivity in IRS suffering patients and thus to correct the dyslipidaemia which is considered to cause the accelerated progress of atherosclerosis. However, currently this is not a universally well defined disease.

The present invention relates to a crystalline solid form of the compound of formula I. Significant advantages can arise when the compound of formula I can be isolated in a crystalline form, for example, in the manufacture of the compound to the purity levels and uniformity required for regulatory approval and for ease and uniformity of formulation.

We have isolated the compound of formula I as a crystalline solid. The particular crystalline form isolated exists in a form which is substantially or essentially free of solvent (hereinafter referred to as "the anhydrous form"). Alternatively a solvated form may be produced, for example, a hydrated form.

We present as a feature of the invention a crystalline form of a compound of formula I, or a solvate thereof. In an alternative feature of the invention we present a crystalline form of a pharmaceutically-acceptable salt of the compound of formula I, or a solvate thereof.

By the use of the term "solvated" we also include hydrated. By the use of the term "a crystalline form" we mean each and everyone possible crystalline form of the compound of formula I, preferably an anhydrous form.

A crystalline form of the compound of formula I can be defined by reference to its melting point, powder X-ray diffraction pattern and single-crystal X-ray data.

The melting point of the crystalline form of the compound of formula I generally depends on the level of purity and may be determined by conventional procedures well known in the art, for example, by differential scanning calorimetry (DSC). Typically, the anhydrous form has a melting point which is in the range 82–92° C., for example about 85–89° C.

The anhydrous form has an X-ray powder diffraction pattern containing specific peaks of high intensity at 6.2, 4.47 and 4.15 Å. Additional specific peaks of lower relative intensity to the first peaks are at 4.69, 3.64, 3.60 and 3.45 Å.

A crystalline form of a compound of formula I may be obtained from a non-crystalline form of a compound of formula I, by crystallisation from a suitable solvent (including organic solvents, aqueous solutions and mixtures thereof), such as toluene and ethyl acetate, or a mixture of solvents, such as a mixture of ethanol/water, isopropanol/water or toluene/isooctane. To initiate crystallisation seeding with crystalline compound of formula I may be required. Crystallisation of the compound from an appropriate solvent system may be achieved by attaining supersaturation, for example, by cooling, by solvent evaporation and/or by the addition of an anti-solvent (a solvent in which the compound of formula I is poorly soluble, examples of suitable antisolvents include heptane or isooctane). Crystallisation temperatures and times will vary depending upon the concentration of the compound of formula I in solution, the solvent system used and the method of crystallisation adopted.

A crystalline form of the compound of formula I may be isolated using techniques well known to those skilled in the art, for example, by decanting, filtration or centrifuging. Similarly the crystalline form may be dried in accordance with well known procedures.

Optional recrystallisation step(s) may be performed using the same or different solvent systems to reduce further impurities, such as amorphous material, chemical impurities, or to convert the crystalline form into a solvated/hydrated form or an anhydrous form.

Preferably crystallisation is carried out directly from the reaction solution. Alternatively crystallisation is performed from a subsequent solution.

A further feature of the invention is a process for the production of a crystalline form of a compound of formula I which comprises crystallising the compound of formula I.

By the use of the term "the anhydrous form", we do not exclude the presence of some solvent, including water, within the crystal lattice structure. Solvent, including water, may also be present outside the crystal lattice structure.

A feature of the invention is a crystalline form of a compound of formula I, as described above, for use in medical therapy.

According to a further feature of the invention there is provided a pharmaceutical composition which comprises a crystalline form of a compound of formula I, as described above, in association with a pharmaceutically-acceptable diluent or carrier. The use of a crystalline form of a compound of formula I, as described above, in the preparation of a pharmaceutical composition by bringing into association a crystalline form of a compound of formula I with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of the crystalline form of a compound of formula I, as described above, that is combined with one or more excipients to produce a single dosage form will necessarily vary depending upon the host treated and the particular route of administration.

For example, a formulation intended for oral administration to humans will generally contain, for example, from 0.001 mg to 50 mg of active agent mixed with an appropriate and convenient amount of excipient(s) which may vary from about 10 to about 99.9999 percent by weight of the total composition.

The invention also includes the use of the crystalline compound of the invention, as described above in the production of a medicament for use in:
 (i) treating dyslipidaemia;
 (ii) treating type 2 diabetes mellitus;
 (iii) treating hyperglycaemia;
 (iv) treating hyperinsulinaemia;
 (v) treating hyperlipidaemia;
 (vi) treating arterial hypertension; and/or
 (vii) treating abdominal obesity.

The invention also includes a method of producing an effect as defined hereinbefore or treating a disease or disorder as defined hereinbefore which comprises administering to a warm-blooded animal, preferably a human, requiring such treatment an effective amount of a crystalline form of a compound of formula I, as described above.

The size of the dose for therapeutic or prophylactic purposes of a crystalline form of a compound of formula I will naturally vary according to the nature and severity of the medical condition, the age and sex of the animal or patient being treated and the route of administration, according to well known principles of medicine.

Suitable daily doses of the compounds of the invention in the therapeutic treatment of humans are about 0.001–50 mg/kg body weight, preferably 0.01–10 mg/kg body weight.

A crystalline form of the compound of formula I may be administered as a sole therapy or it may be administered in conjunction with other pharmacologically active agents such as a anti-diabetic, anti-hypertensive, diuretic or anti-hyperlipidaemic agent.

Crystalline forms prepared in accordance with the Example(s) below showed essentially the same powder X-ray diffraction patterns and/or DSC thermograms. It was clear when comparing the relevant patterns/thermograms (allowing for experimental error) that the same crystalline form had been formed. DSC onset temperatures may vary in the range ±5° C. (for example ±2° C.), and powder X-ray diffraction pattern distance values may vary in the range ±5 on the last decimal place.

Abbreviations
 EtOAc=ethyl acetate
 HPLC=high-pressure liquid chromatography
 i-PrOAc=isopropyl acetate
 NMP=N-methyl-2-pyrrolidinone
 THF=tetrahydrofuran Synthesis of (S)2-Ethoxy-3-[4-(2-{4-methanesulfonyloxyphenyl}ethoxy)phenyl] propanoic Acid 1) Ethyl (S)-2-Ethoxy-3-(4-hydroxyphenyl)propanoate
 a) Preparation of Ethyl 2-Ethoxyethanoate A solution of 2-chloroacetic acid (50 g, 529 mmol, 1.0 eq) in absolute ethanol (110 ml, 2.2 vol. (where vol. Hereinafter means volume equivalent) was charged to an ethanol solution of sodium ethoxide (494 ml, 90 g, 1.32 mol, 2.5 vol.). The temperature during the charging was kept at 15–25° C. When the charging was completed the temperature was raised to 50° C. The reaction mixture was cooled to 15° C. when >95% conversion was achieved. HCl (g) was then charged until the pH of the mixture was <1. When the conversion was >95% the slurry was cooled to 15° C. and neutralised to pH 5–7 with sodium ethoxide solution (approximately 5–20% of the initially charged amount). After neutralisation the slurry was cooled to 5° C. and ethyl acetate (150 ml, 3 vol.) was charged. The sodium chloride formed in the reaction was then filtered off and washed with ethyl acetate. The solution was then evaporated. Maximum remaining ethanol was 20 w/w %

The overall yield of the subtitle compound was 58% of the theoretical value (loss was in evaporation). The chemical purity was >99%.

Preparation of Ethyl 2-Ethoxy-3-(4-methoxyphenyl) propenoate

4-Methoxybenzaldehyde (100 g, 734 mmol, 1.0 eq.) and ethyl 2-exthoxyethanoate (116 g, 881 mmol, 1.2 eq.) was dissolved in THF (600 ml, 6 vol.) under an atmosphere of nitrogen. The solution was cooled to −20° C. To the resulting solution, a solution of potassium tert-butoxide (98.8 g, 880 mmol, 1.2 eq) in THF (704 ml, 7.1 vol. corresponding to potassium tert-butoxide) was slowly charged while maintaining the temperature <−10° C. After the charging was completed, the reaction mixture was stirred for 1 hour at a temperature of −50° C. to −10° C. To the slurry, was then charged with glacial acetic acid (53 g, 1.24 mol, 1.7 eq.) maintaining the temperature at <+5° C. The THF was then evaporated until about ⅓ remained. Toluene (824 ml, 8.24 vol.) was added and the rest of the THF evaporated. Water (200 ml, 2 vol.) and methanesulfonic acid (50 ml, 0.5 vol.) were added to the toluene slurry to give a pH in the water layer of 2–3. The water layer was separated off. The toluene layer was then evaporated to remove the remaining water. To the toluene solution was added methanesulfonic acid (2.11 g, 22 mmol, 0.03 eq). The toluene solution was refluxed with a Dean-Starke device connected until full conversion was achieved. The solution was cooled to 25° C. The solution was then washed with sodium hydroxide (aq., 48%) (1.83 g, 22 mmol, 0.03 eq.) diluted in water (15 ml).

The overall yield of the subtitle compound was approximately 52% of the theoretical value.

c) Preparation of 2-Ethoxy-3-(4-methoxyphenyl) propenoic Acid

NaOH (aq., 48%) (122 g, 1.46 mol, 2.0 eq.), water (244 ml, 2.44 vol.) and EtOH (90 ml, 0.9 vol.) were charged to the toluene solution of ethyl 2-ethoxy-3-(4-methoxyphenyl) propenoate (approximately 96 g, 382 mmol, 0.52 eq.). The reaction mixture was heated to 50° C. and stirred until full conversion was achieved. After the reaction was complete, the toluene layer was separated off and the water layer was then washed with toluene (100 ml, 1 vol.). After separation, the water layer was cooled to +5° C. and acidified with conc. HCl (approximately 173 ml, 2.1 mol, 2.9 eq.). The temperature was kept <10° C. during the charging of the acid. EtOAc (100 ml, 1 vol.) was added to the acidic water slurry. After extraction the phases were separated. The EtOAc solution was evaporated and toluene (288 ml, 3 vol.) was added.

The toluene solution was seeded with 2-ethoxy-3-(4-methoxyphenyl) propenoic acid and cooled to 0° C. After crystallisation the material was filtered. The wet substance was used without drying in the subsequent step.

The overall yield of the subtitle compound was 42% of the theoretical value for step b) and c) together. The chemical purity was 99.7 %.

d) Preparation of 2-Ethoxy-3-(4-methoxyphenyl) propanoic Acid

Palladium on charcoal (5%, 60% water wet) (13.2 g, 0.26 g Pd, 2.44 mmol Pd, 0.0054 eq.) was charged to a solution of 2-ethoxy-3-(4-methoxyphenyl) propenoic acid (100 g, 450 mmol, 1.0 eq.) in ethanol (800 ml, 8 vol.) under a nitrogen atmosphere. The vessel was then pressurised with hydrogen to 4 bar total pressure. The hydrogenation was continued until full conversion was achieved. The catalyst was filtered off and the ethanol was evaporated under vacuum. Toluene (500 ml, 5 vol.) was added and then evaporated off. The residue was dissolved in toluene (500 ml, 5 vol.) and evaporated to a volume of 260 ml. The solution was heated to 50° C. and isooctane (800 ml, 8 vol.) was added. The solution was cooled to 35° C. and then seeded with 2-ethoxy-3-(4-methoxyphenyl) propanoic acid.

The temperature was maintained at 35° C. for 30 min. The thin slurry was then cooled at a rate of 10° C./hour down to +5° C. which was maintained overnight. The crystals were then filtered off and washed with isooctane (220 ml, 2.2 vol.) The crystals were dried under vacuum at 30° C.

The yield of the subtitle compound was 88% of the theoretical value. The chemical purity was 99.8 %.

e) Preparation of (1S)-1-(1-Naphthyl)-1-ethanaminium (2S)-2-ethoxy-3-(4-methoxyphenyl)propanoate A solution of 2-ethoxy-3-(4-methoxyphenyl) propionic acid (100 g, 446 mmnol, 1.0 eq.) in i-PrOAc (2000 ml, 20 vol.) was stirred at 0–5° C. under a nitrogen atmosphere. (S)-1-(1-naphthyl) ethylamine (45.8 g, 268 mmol, 0.6 eq.) was added to the resulting solution. The resulting suspension was heated to 75–80° C. to dissolve all particles, thereby achieving a solution. The solution was then cooled and seeded with (2S)-2-ethoxy-3-(4-methoxyphenyl) propanoic acid (S)-1-(1-naphthyl) ethylamine salt. The desired diastereomeric salt was collected by filtration. The crystals were washed with i-PrOAc.

The (2S)-2-ethoxy-3-(4-methoxyphenyl) propanoic acid (1S)-1-(1-naphthyl) ethylamine salt obtained (67 g, 169 mmol, 1.0 eq.) was dissolved by heating to 75–80° C. in i-PrOAc (1340 ml, 20 vol.). The product obtained was collected by filtration, washed with i-PrOAc and dried under vacuum, at 40° C., to a constant weight.

The overall yield over the two crystallisation steps was 74% of the theoretical value. The chemical purity was >99%. The enantiomeric excess (e.e.) was 97.8%.

f) Preparation of (S)-2-Ethoxy-3-(4-hydroxyphenyl) propanoic Acid (2S)-2-Ethoxy-3-(4-methoxyphenyl) propanoic acid (1S)-1-(1-naphthyl) ethylamine salt (100 g, 253 mmol, 1.0 eq.) was suspended in toluene. The mixture was then treated with NaOH (11.1 g, 278 mmol, 1.1 eq.) in water (280 ml, 5 vol.). The upper toluene layer containing the chiral amine was separated. The lower aq. layer was washed with two more portions of toluene (280 ml, 5 vol.). The lower aq. layer was acidified to pH=1 with aq. 37% HCl (30 g, 304 mmol, 1.2 eq.). The water solution containing (S)-2-ethoxy-3-(4-methoxyphenyl) propanoic acid was extracted with two portions of EtOAc (280 ml, 5 vol.). The combined EtOAc extract was washed with one portion of water (280 ml, 5 vol.). The solvent was replaced with NMP under reduced pressure.

NaOH (beads) (45.5 g, 1.14 mol, 4.5 eq.) and octanethiol (129 g, 154 ml, 884 mmol, 3.5 eq.) were charged to the solution of (S)-2-ethoxy-3-(4methoxyphenyl) propanoic acid (approximately 56.6 g, 253 mmol, 1.0 eq.) in NMP (680 ml, 12 vol.) under a nitrogen atmosphere. The reaction mixture was heated to 120° C. and kept at 115–125° C. until the reaction was complete as determined by HPLC.

The reaction mixture was cooled to 60° C. and then quenched with water. The pH was then adjusted to 2–3 with conc. HCl. The temperature was maintained at 60–70° C. Two layers were formed, the upper layer of which containing mainly octanethiol and the corresponding methyl ether (formed in the reaction). The layers were separated and the layer containing water and NMP was concentrated to 34 volumes under vacuum at 80–100 ° C. inner temperature.

The residue was extracted with a mixture of $H_2O$:EtOAc. The EtOAc solution was subsequently washed 3 times with a 15% NaCl solution.

The EtOAc was evaporated and the residue was directly used in the subsequent step or could also be crystallised from toluene to yield a white solid.

The yield was 52% using crystallisation, 90% using only evaporation. The chemical purity was 99.8%. The enantiomeric excess (e.e.) was 97.8%.

g) Preparation of Ethyl (S)-2-Ethoxy-3-(4hydroxyphenyl) propanoate (S)-2-Ethoxy-3-(4-hydroxyphenyl) propanoic acid (874 g, 4.16 mol, 1.0 eq.) was dissolved in EtOAc (1250 ml). To this solution were charged ethanol (3000 ml) and HCl (37%, aq.) (40 ml, 0.48 mol, 0.12 eq.). The solution was heated to boiling (about 72° C.) and water/EtOAc/EtOH (2000 ml) was distilled off. Another portion of EtOH (2000 ml) was charged and another 2000 ml was distilled off. This procedure was repeated once more. At this point approximately 95% conversion was reached. Then EtOH (99.5%, 1000 ml) was added and evaporated off. This was repeated until a conversion of >97.5% was achieved. The solution was then concentrated to a volume of 1700–2000 ml under vacuum and then cooled to 20° C.

The EtOAc solution containing ethyl (S)-2-ethoxy-3-(4-hydroxyphenyl) propanoate was then charged slowly (30–40 min) under vigorous stirring to a solution of NaHCO$_3$ (7% w/w, 3500 ml). Crystallisation occurred after a few minutes. After charging, the slurry was cooled to 0–5° C. and then stirred at 0–5° C. for at least one hour. The crystals were then filtered off and dried under vacuum.

The yield was about 93%. The chemical purity was >99%. The enantiomeric excess (e.e.) was >97.8 %.

2) 2-(4-(Methanesulfonyloxyphenyl) ethylmethanesulfonate 2-(4-Hydroxyphenyl)ethanol (356 g, 2.58 mol, 1.0 eq) was dissolved in methylene chloride (3500 ml) and triethyl amine (653 g, 6.44 mol, 2.5 eq). The mixture was cooled to −20° C. Methanesulfonyl chloride (657 g, 5.74 mol, 2.2 eq) was then added keeping the temperature between −25° C. and −15° C. When the conversion was >95%, the salt formed during the reaction was filtered off and washed with methylene chloride (600 ml). The organic layer was washed first with saturated sodium hydrogencarbonate solution (700 ml) at 20° C. followed by water (700 ml). The methylene chloride was evaporated and replaced by acetonitrile. The acetonitrile solution was then used in the subsequent step.

3) Ethyl (S)-2-ethoxy-3-[4-(2-{4-methanesulfonyloxyphenyl}ethoxylphenyl] propanoate Ethyl (S)-2-ethoxy-3-(4-hydroxyphenyl) propanoate(325 g, 1.34 mol, 1.0 eq) was dissolved in acetonitrile (2600 ml). When a homogenous solution was formed, potassium carbonate (560 g, 4.05 mol, 3.0 eq) and magnesium sulfate (110 g, (0.2 g/g K$_2$CO$_3$)) was added. The acetonitrile solution of 2-(4-(methanesulfonyloxyphenyl)ethylmethanesulfonate (total volume ca: 2050 ml (0.3 g/ml, 2.21 mol, 1.65 eq)) was charged to the reaction vessel and the mixture allowed to react at reflux, 82° C. for 24 hours with vigorous stirring, keeping the volume constant by portion-wise addition of acetonitrile. When a conversion >98% was reached the reaction was cooled to room temperature. The remaining salts were filtered off and washed with acetonitrile (800 ml). The filtrate was evaporated to dryness. The residue was then used in the subsequent step.

4) (S)-2-Ethoxy-3-[4-(2-{4-methanesulfonyloxyphenyl}ethoxy)phenyl] propanoic Acid To the oil of ethyl (S)-2-ethoxy-3-[4(2-{4-methanesulfonyloxyphenyl}ethoxy)phenyl]propanoate (723 g (71.2% assay), 1.18 mol. 1.0 eq) was added THF (3900 ml). When a homogenous solution was formed, water (900 ml) was added. The mixture was cooled to +10° C. Lithium hydroxide solution (390 ml, 4 M, 1.32 eq) was added over 1 hour. The temperature was then raised to +30° C. and the reaction allowed to proceed at this temperature for 2–3 hours. The reaction was stopped when the conversion was >99%. EtOAc (500 ml) was added and the mixture cooled to room temperature. The solution was stirred for about 30 minutes and the THF was evaporated off. When about 80–90% of the THF was evaporated, water (1900 ml) was added. The evaporation was continued until no THF remained in the mixture. The alkaline water solution was then washed with EtOAc (1000 ml, 2×1250 ml, and 950 ml). The pH of the water solution of (S)-2-ethoxy-3-[4(2-{4-methanesulfonyloxyphenyl}ethoxy)phenyl]propanoic acid was then adjusted to 2.0–2.5 with HCl (aq) (550 ml, 3.0 M). EtOAc (2500 ml) was added and the phases separated. The ethyl acetate solution of (S)-2-ethoxy-3-[4-(2-{4-methanesulfonyloxyphenyl}ethoxy)phenyl]propanoic acid was then washed with water (700 ml) and after separation evaporated to dryness. The remaining oil was then used in the following crystallisation.

Crystallisation of (S)-2-ethoxy-3-[4-(2-{4-methanesulfonyloxyphenyl}ethoxy)phenyl] propanoic Acid The crude material from 3 batches of (S)-2-ethoxy-3-[4-(2-{4-methanesulfonyloxyphenyl}ethoxy)phenyl]propanoic acid (1871 g total weight, 1262 g compound, 3.09 mol, 1.0 eq) containing EtOAc (500 ml) was dissolved in toluene (5000 ml) at 50° C. When a clear solution was achieved the solution was evaporated to decrease the amount of EtOAc present. The volume before evaporation was 6750 ml. Another portion of toluene (2500 ml) was added, volume after addition was 7750 ml, and evaporation was continued. A third portion of toluene (2500 ml) was then added to the solution, the volume before the addition was 6300 ml, the volume after the addition was 8800 ml. The evaporation was continued until an opaque solution was formed, volume 8200 ml. Isooctane (1000 ml) was added to the solution which had been heated to 40° C. The crystallisation was initiated by seeding at 40° C. The mixture was vigorously stirred until a slurry was formed. The agitation rate was then decreased. The slurry was left crystallising over night. The slurry was then filtered and washed with toluene:isooctane 5:1 (1800 ml). The crystals were then dried under reduced pressure at 40° C.

Recrystallisation of (S)2-ethoxy-3-[4-(2-{4-methanesulfonyloxyphenyl}ethoxy)phenyl] propanoic Acid (S)-2-Ethoxy-3-[4(2-{(4methanesulfonyloxyphenyl}ethoxy)phenyl]propanoic acid (1040 g (96.4% assay), 2.45 mol, 1.0 eq) was dissolved in toluene (7000 ml) at a temperature of 60° C. When a clear solution was achieved isooctane (1720 ml) was added to the solution. The solution was then filtered through Silica 60 gel. The solution was then cooled from 50° C. to 45° C., at this temperature crystallisation occurred. The slurry was cooled to 20° C. The solid was then filtered and washed with toluene:isooctane 5:1(1500 ml). The crystals were dried under reduced pressure at 40° C.

Melting Point Determination

Differential scanning calorimetry (ISC) was performed using a Mettler DSC820 instrument, according to standard methods, for example those described in: Höhne, G. W. et al (1996), *Differential Scanning Calorimetry*, Springer, Berlin. DSC of the anhydrous form showed an endotherm with an extrapolated onset temperature of ca 87° C. (ca 102 J/g)

X-ray Powder Diffraction Pattern Determination

The X-ray powder diffractograms (XRPD) were determined using a Siemens D5000 X-ray diffractometer and/or a Philips X'Pert MPD X-ray diffractometer. XRPD was performed on samples prepared according to standard methods, for example those described in: Giacovazzo, C. et al (1995), *Fundamentals of Crystallography*, Oxford University Press; Jenkins, R. and Snyder, R. L. (1996), *Introduction to X-Ray Powder Diffractometry*, John Wiley and Sons, New York; Bunn, C. W. (1948), *Chemical Crystallography*, Clarendon Press, London; or Klug, H. P. and Alexander, L. E. (1974), *X-Ray Diffraction Procedures*, John Wiley and Sons, New York.

The crystals of an anhydrous form were analyzed by XRPD and the results tabulated below in Table 1 (in which RI represents relative intensity). The diffractogram was measured with variable slits and without internal standard. The intensities were based on the intensities observed in a variable slit measurement without background subtraction. The relative intensities are less reliable, and instead of numeric values, the following definitions are used:

| % Relative Intensity | Definition |
|---|---|
| 25–100 | vs (very strong) |
| 10–25 | s (strong) |
| 3–10 | m (medium) |
| 1–3 | w (weak) |

Some additional weak or very weak peaks found in the diffractogram have been omitted from Table 1.

TABLE 1

X-ray powder diffraction data for an anhydrous form of a crystalline form of a compound of formula I.

| d-value/Å | RI | d-value/Å | RI | d-value/Å | RI |
|---|---|---|---|---|---|
| 12.3 | w | 3.64 | s | 2.74 | w |
| 9.4 | m | 3.60 | s | 2.72 | m |
| 7.2 | m | 3.56 | m | 2.67 | w |
| 6.9 | m | 3.45 | s | 2.60 | w |
| 6.2 | vs | 3.43 | m | 2.45 | w |
| 5.3 | m | 3.35 | w | 2.35 | w |
| 5.2 | w | 3.29 | w | 2.31 | w |
| 4.90 | w | 3.26 | m | 2.20 | w |
| 4.69 | s | 3.17 | w | 2.18 | w |
| 4.47 | vs | 3.12 | m | 2.11 | w |
| 4.42 | m | 3.10 | w | 2.08 | w |
| 4.22 | m | 3.03 | w | 2.02 | w |
| 4.15 | vs | 2.95 | w | 1.99 | w |
| 4.08 | w | 2.85 | w | 1.93 | w |
| 3.95 | w | 2.80 | m | | |
| 3.79 | w | 2.78 | w | | |

It will be understood that the d-values of the X-ray powder diffraction patterns may vary slightly from one instrument to another and so the values quoted are not to be construed as absolute. It is reasonable to assume that a crystalline form of a compound of formula I is that which is described herein if the d-values are within ±5 on the last decimal place, especially if within ±2 on the last decimal place.

Single Crystal X-Ray Diffraction Pattern Determination

A unit cell was determined from single crystal X-ray data of the anhydrous form. It was orthorhombic with $P2_12_12_1$ symmetry, Z=4, and the following dimensions: $a=5.762$ Å, $b=14.426$ Å, $c=24.785$ Å, $\alpha=\beta=\gamma=90°$ and $V=2060.2$ Å$^3$.

What is claimed is:

1. A crystalline form of the compound (S)-2-ethoxy-3-[4-(2-{4-methanesulfonyloxyphenyl}ethoxy)phenyl]propanoic acid, shown in formula I below,

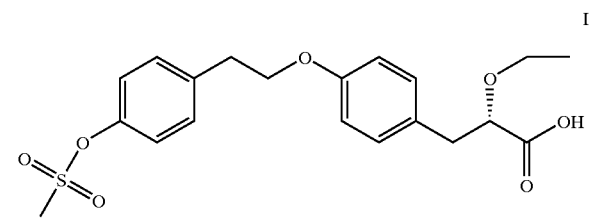

which is substantially or essentially free of solvent and which has a melting point of between 82 and 92° C., an X-ray powder diffraction pattern containing specific peaks of high intensity at 6.2, 4.47 and 4.15 Å, and additional specific peaks of lower relative intensity to the first peaks at 4.69, 3.64, 3.60 and 3.45 Å.

2. A pharmaceutical formulation comprising a crystalline form of a compound of formula I, as defined in claim 1, and a pharmaceutically acceptable adjuvant, diluent or carrier.

3. A method for treatment or prophylaxis of conditions associated with reduced sensitivity to insulin, which method comprises administering a therapeutically effective amount of a compound according to claim 1 to a patient having such reduced sensitivity to insulin.

4. A method for treatment or prophylaxis of a disorder selected from the group consisting of dyslipidaemia, type 2 diabetes mellitus, hyperglycaemia, hyperinsulinaemia, arterial hypertension, abdominal obesity and any combination thereof, which method comprises administering a therapeutically effective amount of a compound according to claim 1 to a patient in need of such treatment or prophylaxis.

5. A process for the preparation of a crystalline form of the compound of formula I according to claim 1 from a non-crystalline form, which comprises dissolution of the non-crystalline compound in an appropriate solvent system followed by crystallization of the non-crystalline compound from the solvent system by attaining supersaturation, by solvent evaporation and/or by addition of an anti-solvent.

* * * * *